United States Patent [19]

Labes et al.

[11] Patent Number: 5,328,998

[45] Date of Patent: Jul. 12, 1994

[54] PROMOTER SCREENING VECTOR, STREPTOMYCES PROMOTERS FOUND THEREWITH, AND THE ISOLATION AND USE THEREOF

[75] Inventors: Gabriele Labes; Wolfgang Wohlleben, both of Bielefeld, Fed. Rep. of Germany

[73] Assignee: Hoechst Aktiengesellschaft, Frankfurt am Main, Fed. Rep. of Germany

[21] Appl. No.: 925,920

[22] Filed: Aug. 7, 1992

[30] Foreign Application Priority Data

Aug. 9, 1991 [DE] Fed. Rep. of Germany ....... 4126415

[51] Int. Cl.⁵ .................. C07H 21/04; C12N 15/76; C12N 15/74
[52] U.S. Cl. .................. 536/24.1; 435/5; 435/6; 435/235.1; 435/320.1; 435/69.1; 536/22.1; 536/23.72
[58] Field of Search ............. 435/320.1, 69.1; 536/27, 24.1

[56] References Cited

U.S. PATENT DOCUMENTS 4,918,015 4/1990 Wohlleben et al. ............. 435/172.3

OTHER PUBLICATIONS

Nazarov et al., Biotechnology Letters, vol. 12 (9): 639-644, 1990.
Gurthrie et al., J. Bact. 172 (11): 6189-6193, 1990.
Mervyn J. Bibb and Gary R. Janssen, *Unusual Features of Transcription and Translation of Antibiotic Resistance Genes in Antibiotic-Producing Streptomyces*, in Fifth International Symposium on the Genetics of Industrial Microorganisms 309-318 (M. Alacevic et al. eds., 1986).
B. K. Leskiw et al., "TTA Codons in Some Genes Prevent Their Expression in a Class of Developmental, Antibiotic-Negative, Streptomyces Mutants," Proc. Natl Acad. Sci. U.S.A., vol. 88, pp. 2461-2465 (1991).
Wolfgang Wohlleben et al., "On the Evolution of Tn21-like Multiresistance Transposons: Sequence Analysis of the Gene (aacCl) for Gentamicin Acetyltransferase-3-I(AAC(3)-I), Another Member of the Tn21-based Expression Cassette," Mol. Gen Genet., vol. 217, pp. 202-208 (1989).

*Primary Examiner*—Margaret Parr
*Assistant Examiner*—Paul B. Tran
*Attorney, Agent, or Firm*—Finnegan, Henderson, Farabow, Garrett & Dunner

[57] ABSTRACT

The invention relates to a promoter screening vector, to methods for the identification and isolation of *Streptomyces* promoters using the screening vector, and to the isolated promoters themselves, preferably the pS1 and p14 (SEQID NO: 1) promoters of the *S. ghanaensis* phase I19.

2 Claims, 5 Drawing Sheets

```
  1 TCGAATCAGCCGGATTCGCGGAAGACGTACAGGTGCACTGGAAGCCTGTAGAGACCTTCG
    AGCTTAGTCGGCCTAAGCGCCTTCTGCATGTCCACGTGACCTTCGGACATCTCTGGAAGC
    1 TAQI, 3 HINFI, 10 HPAII, 13 HINFI, 17 FNUDII, 21 MBOII, 25
    MAEII, 27 RSAI, 33 HGIAI SDUI SDUI, 58 TAQI,

61 ATGGATGAGCAATCGAGAAGTAAGCACACCGGGCGGATTTCCGCCAAGCTTCCTATCCAG
    TACCTACTCGTTAGCTCTTCATTCGTGTGGCCCGCCTAAAGGCGGTTCGAAGGATAGGTC
    63 FOKI, 73 TAQI, 89 HPAII NCII SCRFI, 106 HINDIII, 107 ALUI, 117
    APYI ECORII SCRFI,

121 GAGATATTATGAGTTACGTAGACCTACGCCTTGACCTTGATGAGGCGGCGTGAGCTACAA
    CTCTATAATACTCAATGCATCTGGATGCGGAACTGGAACTACTCCGCCGCACTCGATGTT
                                  -35II    -35I              -10II
    133 MAEIII, 135 SNABI, 136 MAEII, 138 ACCI, 162 MNLI, 165
    FNUIVHI, 173 ALUI,

181 TCAATACTCGATTAGGTCAAGGTGGAACGCAGAGAGGGTCTGACTGCCTGAGTCGGTAGT
    AGTTATGAGCTAATCCAGTTCCACCTTGCGTCTCTCCCAGACTGACGGACTCAGCCATCA
    -10I                         RBSI
    188 TAQI, 214 MNLI, 228 DDEI, 230 HINFI,

241 CAGGTGATGAGGGAGATAGAGCCAAGCAAAGAGGAGAGGGTCATTGCGGGTTAGTGCTAC
    GTCCACTACTCCCTCTATCTCGGTTCGTTTCTCCTCTCCCAGTAACGCCCAATCACGATG
                                    RBS II
    243 HPHI, 249 MNLI, 263 TTH111II, 271 MNLI,
    276 MNLI,

301 TCGATGTACCTGGAGAGGAGTTCCCCAAACTCCGCCTTCTCGCCCTCTGTCAGGTCGA
    AGCTACATGGACCTCTCCTCAAGGGGTTTGAGGCGGAAGAGCGGGAGACAGTCCAGCT
    301 TAQI, 306 RSAI, 309 APYI ECORII SCRFI, 310 GSUI, 315
    MNLI, 344 MNLI, 355 TAQI,
```

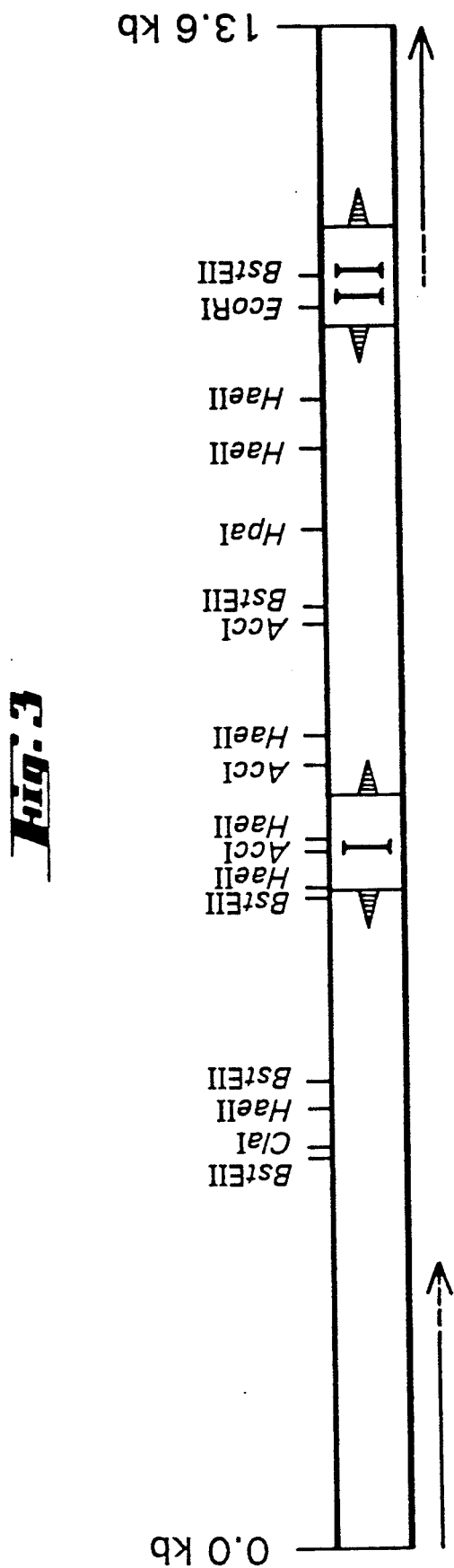

```
  1 TCGAATCAGCCGGATTCGCGGGAAGAGACGTACAGGTGCACTGGAAGCCTGTAGAGACCTTCG
    AGCTTAGTCGGCCTAAGCGCCCTTCTGCATGTCCACGTCCACGTGACCTTCGGACATCTCTGGAAGC
                ^              ^                 ^
    1 TAQI,  3 HINFI, 10 HPAII, 13 HINFI, 17 FNUDII, 21 MBOII, 25
    MAEII, 27 RSAI, 33 HGIAI SDUI SDUI, 58 TAQI,

61 ATGGATGAGCAATCGAGAAGTAAGCACACACCGGGGCGGATTCCGCCAAGCTTCCTATCCAG
    TACCTACTCGTTAGCTCTTCATTCGTGTGGCCCCGCCTAAAGGCGGTTCGAAGGATAGGTC
                                                              ^^
    63 FOKI, 73 TAQI, 89 HPAII NCII SCRFI, 106 HINDIII, 107 ALUI, 117
    APYI ECORII SCRFI,
                                               1
121 GAGATATTATGAGTTACGTAGACCTACGCC|TTGACC|TTGATG|AGGCGGGCGTGAGC|TACAA|
    CTCTATAATACTCAATGCATCTGGATGCGG|AACTGG|AACTAC|TCCGCCACTCG|ATGTT|
                                    -35II      1             -10II
    133 MAEIII, 135 SNABI, 136 MAEII, 138 ACCI, 162 MNLI, 165
    FNUIVHI, 173 ALUI,
                       1                           2        1
181 |TCAATACTCGATTAGGT|CAAGGTGAACGCAGAGAGGGT|CTGAC|TGCCTGAGTCGGTAGT
    |AGTTA|TGAGCTAATCCAGTTCCACCTTGCGTCTCTCCCAGACTGACGGACTCAGCCATCA
     -10I                                  RBSI
    188 TAQI, 214 MNLI, 228 DDEI, 230 HINFI,
                                                2
241 CAGGTGATGAGGGAGATAGAGCCAAGCAAAGAGGAGAGAGGGTCATTGCGGGTTAGTGCTAC
    GTCCACTACTCCCCTCTATCTCGGTTCGTTTCTCCTCTCTCCCAGTAACGCCCAATCACGATG
                                         RBS ^II
    243 HPHI, 249 MNLI, 263 TTH111II, 271 MNLI,
    276 MNLI,

301 TCGATGTACCTGGAGAGGAGTTCCCAAACTCCGCCTTCTCGCCCTCTGTCAGGTCGA
    AGCTACATGGACCTCTCCTCAAGGGTTTGAGGCGGGAAGAGCGGGAGACAGTCCAGCT
    301 TAQI, 306 RSAI, 309 APYI ECORII SCRFI, 310 GSUI, 315
    MNLI, 344 MNLI, 355 TAQI,
```

FIG. 4

```
  1 TCGAGGTAAATACCTCTCTTCGGCTAGTCCTTCGTAATAGTCTTCTGGGTTGTGTAATCGT
    AGCTCCATTTATGGAGAAGCCGATCAGGAAGCATTATCAGAAGACGCCAACACATTAGCA
    1 TAQI,  3 MNLI, 13 MNLI, 15 MBOII, 22 MAEI, 39 MBOII,
 61 CTCTCCTATCGAGCTGCCATCGCGTCCCGCAGATGACGCAGAACAGCTCTGCTCTAGATG
    GAGAGGATAGCTCGACGGTAGCGCAGGGCGTCTACTGCGTCTTGTCGAGACGAGATCTAC
    69 TAQI, 72 AlUI, 73 BBVI FNUIVHI, 81 FNUDII, 82 HHAI, 95 HGAI, 105 AlUI, 113 XBAI, 114 MAEI,
121 TTATCAGAGTACACTCGGTCCACGAATAACCCGGCCGGTGGACTTATTACAGACGCATTGAC
    AATAGTCTCATGTGAGCCAGGTGCTTATTGGGCCGGCCACCTGAATAATGTCGCGTAACTG
    129 RSAI, 135 TAQI, 137 ASUI AVAII, 149 NCII SCRFI, 150 HPAII, 151
    CFRI GDIII XMAIII,  152 HAEIII, 154 HPAII, 171 HHAI, 178 ACYI HGAI,       -'35I'
181 GCCACCCTTATAGGTAACGTCGGTGACCGTGCCAGAGCTACCCGCCTTGTAC
    CGGTGGGAATATCCATTGCAGCCACTGGCGGTCTCGATGGGCGGAACATG
    184 HGIEII, 194 MAEII, 197 MAEII, 202 BSTEII HPHI, 203 MAEIII, 224 AlUI, 237 RSAI,
                                                                  -'10I'  1'
241 GAGGCCAGGGACAGCAGAAGCGAAAGTACCGAAGAAACC
    CTCCGGTCCCCTGTCGCTTCCGCTTCATGGCTTGTTTGG
    241 MNLI, 242 HAEI, 243 HAEIII, 245 APYI ECORII SCRFI, 265 AlUI, 270 NSPBII, 272 BBVI
    FNUIVHI, 287 RSAI, 292 MBOII, 299 HPAII,
    GGACCAATCAAAGTCGAGGATCGCGGCCCCCTCAGTTCCTTCTCGGATACCGGCCGGCGA
    CCTGGTTAGTTTCAGCTCTCGGATCGCCGGGAGTCAAGGAAGAGCCTATGGCCGCT
    301 ASUI AVAII, 314 TAQI, 322 MAEI, 325 FNUIVHI, 327 ASUI HAEIII,
    330 MNLI, 331 DDEI, 341 MBOII, 353 NCII SCRFI, 354 HPAII,
                                              -'10II'
361 CAGATGACCTTTGCCGGTACCCCATCAAGGATTGAGAACCAGGCGTCACCACCTTGATTA
    GTCTACTGGAACGGCATGGGGTAGTTCCTAACTCTTGGTCCGCAGTGGTGGAACTAAT
    RBS
    367 HGIEIII, 374 HPAII, 376 HGICI KPNI NLAIV, 377 RSAI, 399 APYI
    ECORII SCRFI, 402 ACYI, 403 HGAI, 405 MAEIII, 406 HPHI,
421 CTTTCGA
    GAAAGCT
    424 TAQI,
```

FIG. 5

SEQUENCE LISTING ( 1 ) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 358 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:1:

```
TCGAATCAGC CGGATTCGCG GAAGACGTAC AGGTGCACTG GAAGCCTGTA GAGACCTTCG      60
ATGGATGAGC AATCGAGAAG TAAGCACACC GGGCGGATTT CCGCCAAGCT TCCTATCCAG     120
GAGATATTAT GAGTTACGTA GACCTACGCC TTGACCTTGA TGAGGCGGCG TGAGCTACAA     180
TCAATACTCG ATTAGGTCAA GGTGGAACGC AGAGAGGGTC TGACTGCCTG AGTCGGTAGT     240
CAGGTGATGA GGGAGATAGA GCCAAGCAAA GAGGAGAGGG TCATTGCGGG TTAGTGCTAC     300
TCGATGTACC TGGAGAGGAG TTCCCCAAAC TCCGCCTTCT CGCCCTCTGT CAGGTCGA      358
```

(2) INFORMATION FOR SEQ ID NO:2:

(i) SEQUENCE CHARACTERISTICS:
        (A) LENGTH: 427 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

```
TCGAGGTAAA TACCTCTTCG GCTAGTCCTT CGTAATAGTC TTCTGCGGTT GTGTAATCGT      60
CTCTCCTATC GAGCTGCCAT CGCGCTCCGC AGATGACGCA GAACAGCTCT GCTCTAGATG     120
TTATCAGAGT ACACTCGGTC CACGAATACC CGGCCGGTGG ACTTATTACA GCGCATTGAC     180
GCCACCCTTA TAGGTAACGT CGGTGACCGC CGAAGCGTGC CAGAGCTACC CGCCTTGTAC     240
GAGGCCAGGG ACAGCAGAAG CGAAAGCTAC CGCTGCACCA CCAGAAGTAC CGAAGAAACC     300
GGACCAATCA AAGTCGAGAG CCTAGCGGCC CTCAGTTCCT TCTTCTCGGA TACCCGGCGA     360
CAGATGACCT TTGCCGGTAC CCCATCAAGG ATTGAGAACC AGGCGTCACC ACCTTGATTA     420
CTTTCGA                                                              427
```

PROMOTER SCREENING VECTOR, STREPTOMYCES PROMOTERS FOUND THEREWITH, AND THE ISOLATION AND USE THEREOF

BACKGROUND OF THE INVENTION

1. Field of the Invention

The invention relates to a promoter screening vector, to methods for the identification and isolation of *Streptomyces* promoters using the screening vector, and to the isolated promoters themselves, preferably the ps1 (SEQ ID No: 2) and p14 (SEQ ID NO: 1) promoters of the *S. ghanaensis* phage I19 which are described hereinafter.

2. Description of the Prior Art

Only relatively few strong promoters are hitherto available for homologous and heterologous gene expression in *Streptomyces*. The promoters hitherto described and employed for this purpose mainly derive from antibiotic-resistant genes and from other genes whose expression is regulated by other gene products.

In order to be able to utilize *Streptomyces* better as host organism for strong expression of any required gene there is a need for correspondingly strongly constitutive promoters as well as promoters of defined strength. Promoters of these types can be found, for example, in the DNA of lytic bateriophages.

SUMMARY OF THE INVENTION

It has been possible with the aid of the promoter screening vector pGL703 (FIG. 1) to isolate suitable phage promoters.

This screening vector is a shuttle plasmid which harbors the replication regions of the *E. coli* plasmid pACYC184 and of the *Streptomyces* plasmid pSG5. It has the neomycin-resistance gene ($Nm^R$) of Tm5 as selection marker for streptomyces and has the promoterless gentamicin-resistance gene of Tn1696 (GmAp) as new indicator gene. In addition, it has a chloramphenicol-resistance gene ($Cm^R$) as *E. coli* marker. Upstream of the indicator gene there is the transcription terminator of the phage fd and a multiple cloning site (mcs) which has, inter alia, a unique BamHI and ClaI cleavage site. Both restriction sites can be used for shotgun cloning of DNA which has been restricted with the multicutter enzymes Sau3A and TaqI in the case of appropriately modified DNA.

The promoterless gentamicin-resistance gene as essential component has in the 5' coding region two TTA codons which do not occur or occur very rarely in constitutively expressed *Streptomyces* genes. Corresponding expression of the gene, undetectable by a mediated resistance, therefore takes place only when there is an appropriately high m-RNA level in the cell. This is why the indicator gene is particularly well suited for the identification of strong promoters. Another advantage of the screening vector is the possibility of testing promoter-harboring DNA fragments for their activity directly, i.e. without reclonings, in *E. coli*.

An organism which has proven very suitable as donors of promoters is the virulent *S. ghanaensis* phage I19 which has the smallest of all the actinophage genomes described to date, with 13.6 kb (FIG. 2).

The DNA of the I19 phage is in modified forms so that it cannot be subcloned with the conventional multicutter enzyme Sau3A. In this respect a further suitability of the screening vector becomes evident because it has in front of the indicator gene not only a unique BamHI but also a unique ClaI cleavage site which allows subcloning of the phage DNA by means of the alternative multicutter enzyme TaqI. Plasmids with promoter-harboring DNA fragments can be identified by initial selection of the transformants on gentamicin-containing medium and additionally tested for expression of the neomycin-resistance gene. The level of gentamicin resistance and the amount of transcript formed from the isolated promoters are a measure of the promoter strength.

It was possible to identify two promoter-harboring regions on the phage genome (FIG. 3). From them are derived, inter alia, the p14 and pS1 promoters which have different transcription activities. The sequence data for these promoters are listed in FIGS. 4 and 5.

In tests to determine the minimum inhibitory concentration (MIC), the p14 promoter results in gene expression which is about twice as high as with the erm-up promoter (Bibb MJ, Janssen GR (1986) Unusual features of transcription and translation of antibiotic resistance genes in antibiotic-producing Streptomyces. Fifth International Symposium on the Genetics of Industrial Microorganisms, 1986, eds.: Alacevic M, Hranueli D, Toman Z) which is among the strongest *Streptomyces* promoters to date. In contrast to the latter, p14 is also active in *E. coli*. Corresponding MIC tests show an expression rate which is three times higher than with the strong synthetic hybrid promoter tac. *E. coil*-like −10 and −35 consensus regions (I;II) can be identified but have a new type of structure compared with the SEP sequences described to date. The promoter regions are not in tandem arrangement but are directly adjacent (−35,I,II) or partially overlapping (−10,I,II). The distance between the two regions corresponds to 17 (I) or 19 (II) base pairs and is thus in the optimal range. Whereas the -35 regions correspond, apart from one (II) and two (I) base pairs, to the postulated SEP consensus sequence (-TTGaca-), the -10 regions differ more from the consensus sequence in each case. The motif ATCAAT (I) or TACAAT (II) is present therein, and an essential role is assigned to the four bases CAAT. Short direct sequence repetitions (1) and a long repeat (2) of 9basepairs (see table 1) as well as twopotential ribosomebinding sites (RBS I, II) are likewise characteristic of the promoter region. The pS1 promoter, which is not active in *E. coli*, likewise has short sequence repetitions 1, 1', 2, and 2 are a component of a duplication which is six base pairs long. The latter contains the -CAGAAG- motif which possibly has a function in RNApolymerase recognition in the sense of the conventional − 10 promoter regions (I). Upstream from the first potential −10 region (I) there is a −35-like sequence (II). Also identifiable is a very good ribosome binding site (RBS). With regard to the gentamicin expression rate, pS1 is comparable to p14, while in the neomycin resistance test it has only about one quarter of the activity of the erm-up promoter (Bibb M. J. Janssen G. R; Unusual features of transcription and translation of antibiotic resistance genes in antibioticproducing *Streptomyces;* in: Fifth International Symposium on the Genetics of Industrial Microorganisms, 1986, eds.: Alacevic M.; Hranueli D.; Toman Z.). It can be employed on biological safety grounds because it is active only in *streptomyces*.

BRIEF DESCRIPTION OF THE DRAWINGS

Legend to FIG. 1; Promoter screening vector pGL703 "mcs" stands for "multiple cloning site" and contains cleavage sites for the restriction enzymes EcoRI SstI KpnI SmaI PstI HindIII ClaI XbaI BamHI EcoRI SstI KpnI GmΔP means promoterless gentamicin$^R$ gene; Cm$^R$ means chloroamphenicol-resistance gene; Nm$^R$ means neomycinresistance gene; fd stands for the transcription terminator of the phage fd.

Legent to FIG. 2: Restriction map of the I19 phage DNA

The cleavage sites of the individual restriction enzymes are depicted at the top, and the length and position of the individual restriction cleavage fragments for each of the 6 eznymes used at the bottom.

Legend to FIG. 3: Identified promoter regions on the genome of I19

The promoter regions are indicated as I and II in the genome map of I19.

Legend to FIG. 4: DNA sequence of the p14 promoter

Legend to FIG. 5: DNA sequence of the PS1 promoter

DESCRIPTION OF THE PREFERRED EMBODIMENTS

The invention accordingly relates to the pGL 703 promoter screening vector and to vectors with analogous structure which contain the promoterless gentamicin-resistance gene, to methods for isolating promoters with the aid of such vectors, and to the promoters found therewith, preferably p14 and pS1, and finally to the use thereof. The invention is explained further in the following Examples.

EXAMPLE 1

Characterization of the I19 DNA

Figure 1:
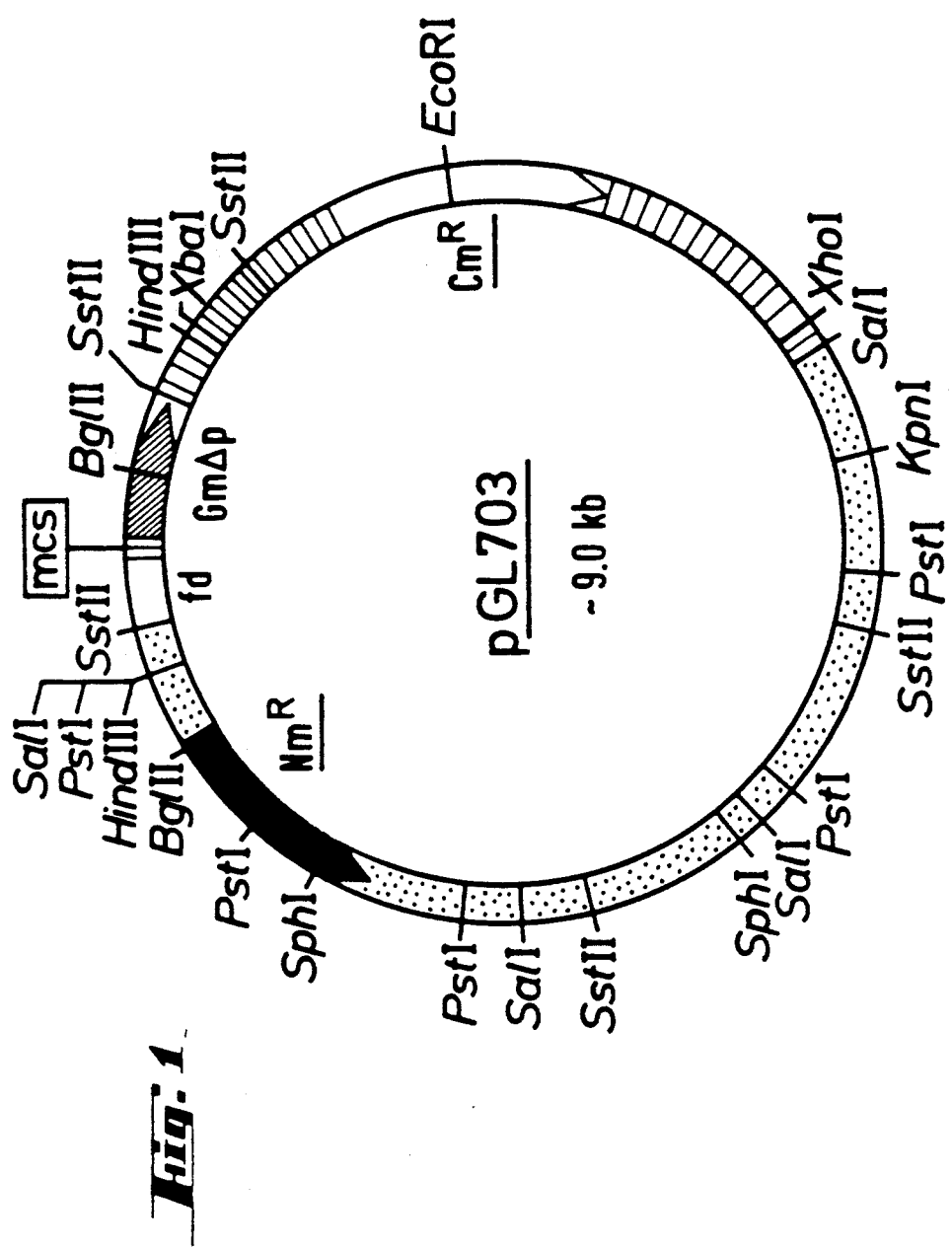
Figure 2:
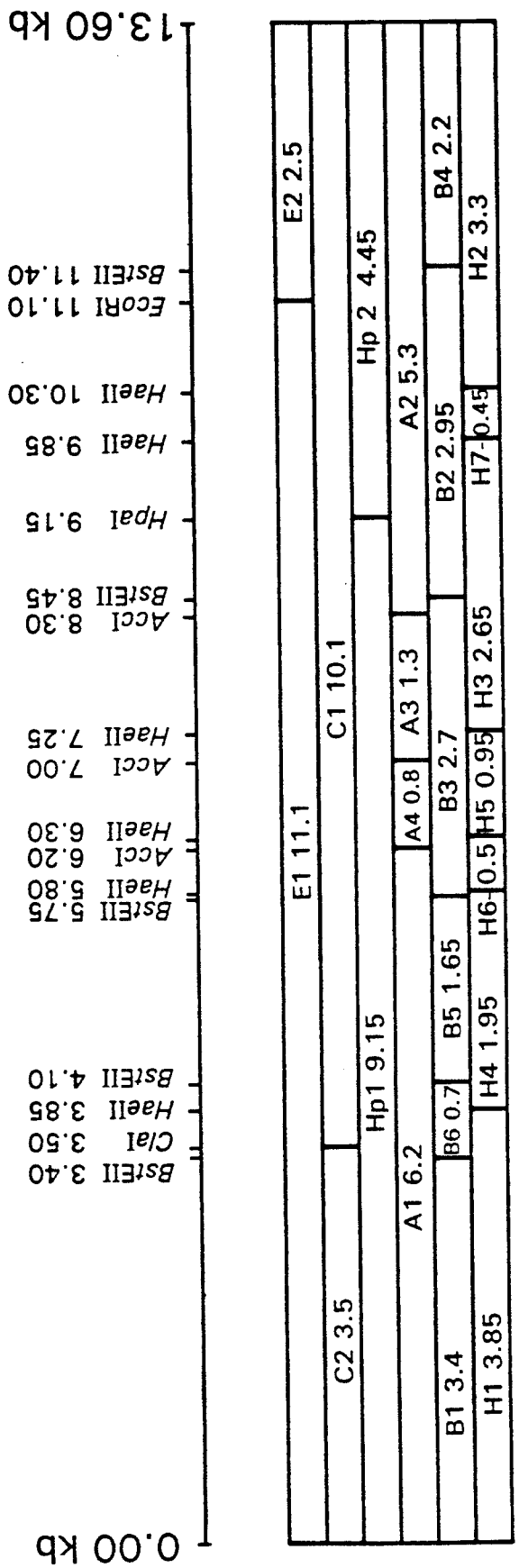

The phage I19 was isolated and characterized as lyric phage (plaques with a diameter of 1.5–2.0 mm) from the bacterium *S. ghanaensis*. Whereas the diameter of the head of the phage (82.8 nm) and the length of the tail (371.8 nm) are in the range of bacteriophages described to date, the I19 DNA is 13.6 kb which is the smallest of all actinophage DNAs hitherto known. Restriction analysis (FIG. 2) revealed that the DNA cannot be cleaved with the enzymes BamHI and Sau3A and is thus present in modified form. It is packaged in the head of the phage as double-stranded linear molecule. Homologous but no cohesive ends were detectable. The phage genome has two promoter regions (FIG. 3, I and II), the strong p14 promoter being in the region II.

EXAMPLE 2

Identification of I19 phage promoters

The DNA of I19, which cannot be fragmented by the enzyme Sau3A was partially cleaved using the alternative multicutter enzyme TaqI to give fragments of length below 1.5 kband was ligated to the pGL703 screening vector cut with ClaI. The ligation mixture was transformed into *S. lividans* TK23 both directly and indirectly via *E. coli*. After direct transformation and covering of the regeneration plates with a gentamicin concentration of 30 μg/ml in the medium it was possible to isolate three gentamicin-resistant TK23 colonies, whereas after previous replication of the hybrid plasmids in the ligation mixture in *E. coli* with subsequent DNA isolation and transformation into *S. lividans* TK23 thirteen gentamicinresistant single colonies were isolated (indirect route). All the selectants obtained in this way proved, as expected, to be Kanamycin resistant in the subsequent test.

EXAMPLE 3

Classification of the I19 promoters

The plasmids of the gentamicin-resistant *Streptomyces* colonies were reisolated, transformed into *E. coli* and characterized in more detail with regard to the insertions therein. It emerged from this that the majority of the isolated promoter-harboring DNA fragments is also active in *E. coli*, i.e. leads to expression of the indicator gene. Also isolated in addition were fragments which display transcription activity only in *Streptomyces*. The isolated I19 promoters were classified by means of these properties and on the basis of the level of gentamicin resistance mediated by the promoters both in *Streptomyces* and in *E. coli* (in the case of the SEP sequences). The highest gentamicin-resistance gene expression rate in both organisms was shown by the p14 promoter as SEP sequence, and in *S. lividans* by the pure *Streptomyces* promoter pS1. The reason for the comparatively low level of resistance of 5–10 mg of μm/ml is the relatively low translation rate of the indicator gene in *Streptomyces*. This is why this screening system is particularly suitable for isolating relatively strong promoters from *Streptomyces* or their bacteriophages. A more accurate characterization of the strengths of the promoters was carried out at the m-RNA level. It was possible in this way to verify the classification carried out initially. Dot-blot analyses in which the yield of Nm m-RNA acted as internal control confirmed that p14 (SEQ ID NO: 1) has the strongest transcription activity of all identified I19 promoters in *S. lividans*.

EXAMPLE 4

Subcloning of the promoters to demonstrate their activity outside the screening vector In order to rule out artifacts such as, for example, sequence constellations from the multiple cloning site of pGL703 and the inserted DNA fragment, which might lead to promoter activity, p14 (SEQ ID NO: 1) and pS1 (SEQ ID NO: 2) were subcloned into the vector pIJ487 (obtainable from the John Innes Foundation, Norwich, England) and selected in *S. lividans* for the expression of the promoterless neomycin gene. It emerged from the subsequent Nm MIC tests that p14 results in twice, and pS1 in this system results in approximately one quarter, the neomycin resistance of the erm-up promoter which is counted in the literature to date among the strongest *Streptomyces* promoters. These results confirm once again the suitability of the new screening vector for isolating particularly strong *Streptomyces* promoters.

---

We claim:
1. The p14 promoter as set forth in SEQ ID NO: 1.
2. The pS1 promoter as set forth in SEQ ID NO: 2.

* * * * *